United States Patent
Bradham et al.

(10) Patent No.: US 10,621,193 B2
(45) Date of Patent: Apr. 14, 2020

(54) DATA MIGRATION FROM A SOURCE SYSTEM TO A DATA SCHEMA OF A MEDICAL STUDY ON A TARGET SYSTEM

(71) Applicant: International Business Machines Corporation, Armonk, NY (US)

(72) Inventors: Walker Bradham, Raleigh, NC (US); Anthony Castrati, Knightdale, NC (US); Jordan S. Simpson, Raleigh, NC (US)

(73) Assignee: International Business Machines Corporation, Armonk, NY (US)

( * ) Notice: Subject to any disclaimer, the term of this patent is extended or adjusted under 35 U.S.C. 154(b) by 282 days.

(21) Appl. No.: 15/678,212

(22) Filed: Aug. 16, 2017

(65) Prior Publication Data

US 2019/0057137 A1    Feb. 21, 2019

(51) Int. Cl.
| | |
|---|---|
| G06F 17/30 | (2006.01) |
| G06F 16/25 | (2019.01) |
| G16H 10/20 | (2018.01) |
| G06F 3/0484 | (2013.01) |
| G06F 3/0482 | (2013.01) |

(52) U.S. Cl.
CPC .......... G06F 16/254 (2019.01); G16H 10/20 (2018.01); *G06F 3/0482* (2013.01); *G06F 3/04847* (2013.01)

(58) Field of Classification Search
USPC ................................. 707/602, 756; 717/168
See application file for complete search history.

(56) References Cited

U.S. PATENT DOCUMENTS

| | | | |
|---|---|---|---|
| 6,795,868 B1 | 9/2004 | Dingman et al. | |
| 6,996,589 B1* | 2/2006 | Jayaram | G06F 16/258 |
| 8,060,553 B2 | 11/2011 | Mamon et al. | |
| 9,450,999 B2 | 9/2016 | Werr | |
| 2010/0299335 A1* | 11/2010 | Gopalakrishnan | G06F 19/00 707/756 |

(Continued)

OTHER PUBLICATIONS

Anonymously; "Method and Apparatus to Perform Automated Data Migration Between Heterogeneous Data Sources"; http://ip.com/IPCOM/000184153D; Jun. 12, 2009; 6 pages.

(Continued)

*Primary Examiner* — Hung T Vy
(74) *Attorney, Agent, or Firm* — Will Stock; Edell, Shapiro & Finnan, LLC

(57) ABSTRACT

An embodiment of the present invention migrates data between source and target systems. Retrieved source data is mapped to corresponding data elements of a data design for a computer implemented scenario on a target system. One or more of the data elements of the data design are stored on the target system in a format different than a format of the retrieved data. Filters and transformations are generated based on the mapping and data design, and the retrieved data are converted to the format of the target system. One or more from a group of the mapping, filters, and transformations is adjusted in response to detecting at least one from a group of modifications to the data design and non-conforming data received from the one or more source systems. The converted data is stored for the corresponding data elements on the target system for use by the computer implemented scenario.

20 Claims, 14 Drawing Sheets

(56) References Cited

U.S. PATENT DOCUMENTS

2011/0296391 A1* 12/2011 Gass .................. G06F 8/36
  717/168
2016/0328442 A1* 11/2016 Waas .................. G06F 16/252

OTHER PUBLICATIONS

Anonymously; "Near Online Migration for Business Critical Packaged Applications"; http://ip.com/IPCOM/000194907D; Apr. 13, 2010; 7 pages.
Anonymously; "Approach for a Business User Consumable Data Mapper Application"; http://ip.com/IPCOM/000228647D; Jun. 26, 2013; 19 pages.
Oracle; "Successful Data Migration"; Oracle White Paper; http://www.oracle.com/successfuldatamigration.pdf.; Oct. 2011; 15 pages.

* cited by examiner

FIG. 4

| Queue Monitor | | | | | | | X |
|---|---|---|---|---|---|---|---|
| Output sets 1105 | Type 1110 | Status 1115 | Date/Time 1120 | Requested by 1125 | Processed 1130 | Log 1135 | Actions 1140 |
| 20170509132658844_output | Import | Complete | YYYY/MM/DD TT:TT:TT | User1 | ☐ | 1 of 1 | ☐ |
| 20170509102048246_output | Import | Failed | YYYY/MM/DD TT:TT:TT | User1 | ☐ | 0 of 1 | ☐ |
| 20170509101920884_output | Import | Failed | YYYY/MM/DD TT:TT:TT | User1 | ☐ | 0 of 1 | ☐ |
| 20170509101200466_output | Import | Complete | YYYY/MM/DD TT:TT:TT | User1 | ☐ | 1 of 1 | ☐ |
| 20170509101104259_output | Import | Complete | YYYY/MM/DD TT:TT:TT | User1 | ☐ | 1 of 1 | ☐ |
| 20170509101018898_output | Import | Complete | YYYY/MM/DD TT:TT:TT | User1 | ☐ | 1 of 1 | ☐ |
| 20170509100856180_output | Import | Complete | YYYY/MM/DD TT:TT:TT | User1 | ☐ | 1 of 1 | ☐ |
| 20170509100704292_output | Import | Complete | YYYY/MM/DD TT:TT:TT | User1 | ☐ | 1 of 1 | ☐ |
| | | | | | | | Close |

FIG.11

DATA MIGRATION FROM A SOURCE SYSTEM TO A DATA SCHEMA OF A MEDICAL STUDY ON A TARGET SYSTEM

BACKGROUND

1. Technical Field

Present invention embodiments relate to data migration, and more specifically, to migrating data from a source system to a data design or schema for a medical clinical trial or study on a target system.

2. Discussion of the Related Art

Extract-Transform-Load (ETL) applications extract data from a source system in one format, and produce transformed data in another format compatible with a target system. The transformed data is subsequently loaded into the target system for processing. However, ETL applications typically require a user to have knowledge of the target data format or specification (e.g., the specific column of a target database table and corresponding properties and/or format). Without the knowledge of the target system specification, the ETL applications are limited with respect to suggesting and validating data mappings between the source and target systems.

SUMMARY

According to one embodiment of the present invention, a system migrates data between source and target systems, and includes at least one processor. The system retrieves data from one or more source systems. The retrieved data is mapped from the source systems to corresponding data elements of a data design for a computer implemented scenario on a target system. One or more of the data elements of the data design are stored on the target system in a format different than a format of the retrieved data. Filters and transformations are generated based on the mapping and data design, and the retrieved data of the source systems are converted to the format for storing the corresponding data elements on the target system. The system adjusts one or more from a group of the mapping, filters, and transformations in response to detecting at least one from a group of modifications to the data design and non-conforming data received from the one or more source systems. The converted data is stored for the corresponding data elements on the target system for use by the computer implemented scenario. Present invention embodiments further include a method and computer program product for migrating data between source and target systems in substantially the same manner described above.

BRIEF DESCRIPTION OF THE DRAWINGS

Generally, like reference numerals in the various figures are utilized to designate like components.

FIG. 4 is a schematic illustration of an example graphical user interface for defining mappings between data elements of a source system and data elements of a data design or schema for a medical clinical trial or study on a target system according to an embodiment of the present invention.

FIG. 11 is a schematic illustration of an example graphical user interface for transactional monitoring according to an embodiment of the present invention.

DETAILED DESCRIPTION

Figure 1:
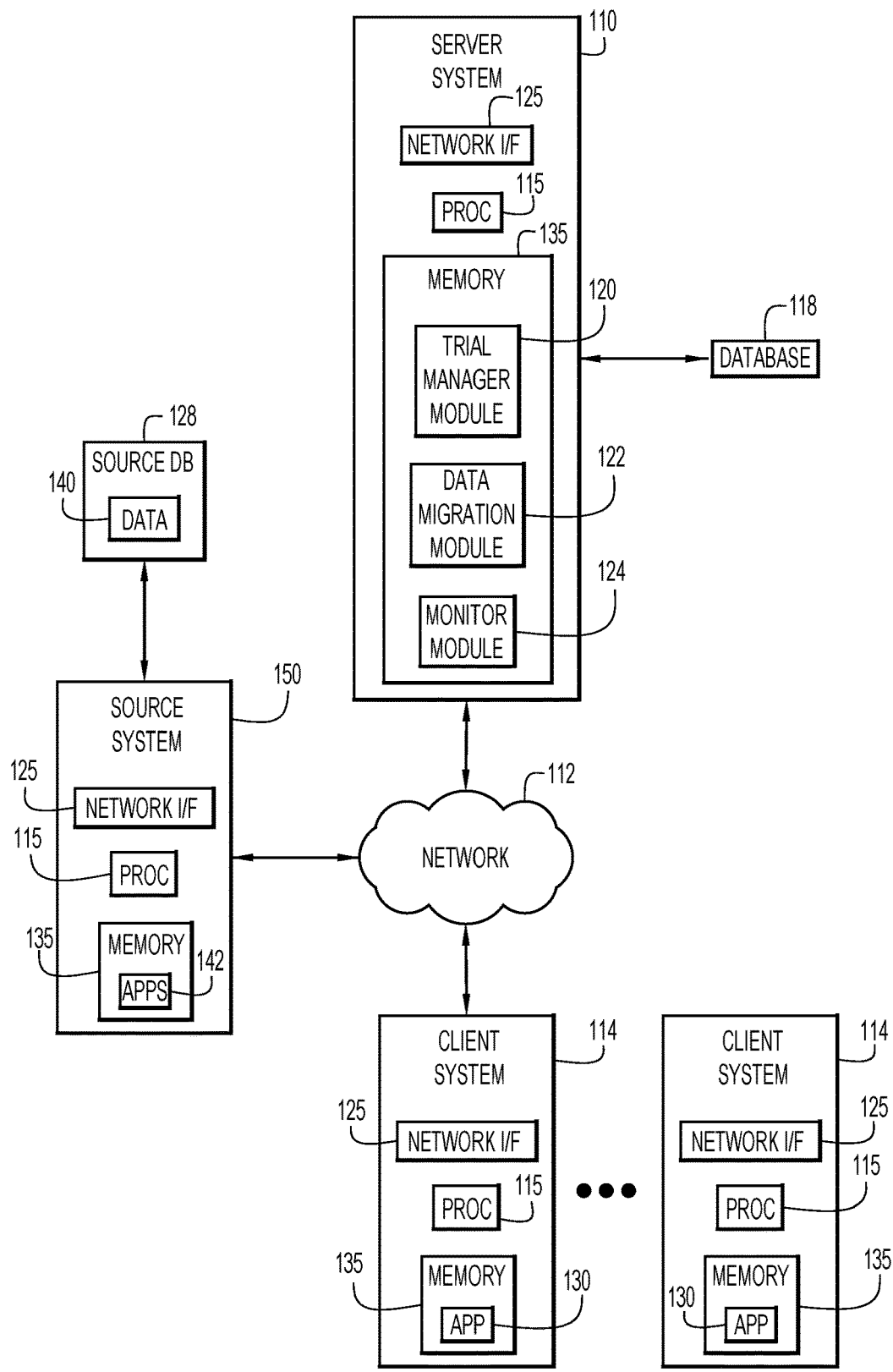
FIG. 1 is a diagrammatic illustration of an example computing environment for use by embodiments of the present invention.

An embodiment of the present invention pertains to an Extract-Transform-Load (ETL) type tool which requires no knowledge of the destination formatting of the data. Initially, a data design or schema for a medical clinical trial or study is created on a target system by a user by specifying (and/or selecting) data elements (and certain corresponding properties) and/or data structures (e.g., tables with columns/fields, etc.) to be used for the medical clinical trial. The target system handles the storage of the user-specified (and/or selected) data elements of the medical clinical trial and underlying details of the database (e.g., specific columns and properties/formats of database tables corresponding to the user-specified data elements and data structures, etc.). For example, a date field in the data design for the medical clinical trial may be specified for a certain table of the data design and with a desired format. However, the date field may be stored in a different format and/or database table in the underlying database. Thus, a user may create the data design for the medical clinical trial without knowledge of the specific details of the underlying database of the target system.

In order to migrate data from a source system to the medical clinical trial of the target system, a user simply matches source data to target destinations in the data design for the medical clinical trial on the target system, and output data is generated that meets specification and matches the data design for the medical clinical trial. In other words, the user maps the source data to a data design of an existing medical clinical trial on the target system (e.g., without regard to the underlying details of the target system database), and an underlying specification is implemented based on the mapping. A data test suite provides objective evidence that source data is being transformed as expected within the context of known test data.

Present invention embodiments provide user interface (UI) mapping of source data to a data design or schema of a medical clinical trial or study, real-time validation of configuration against changes to the data design or schema of the medical clinical trial or study, persistence of groups of datasets via file sets (e.g., a user may group source files into sets of files or file sets), importation to multiple protocols in a multi-tenant, hosted environment, an end-to-end mapping of raw source data to a Clinical Data Interchange Standards Consortium (CDISC) Operational Data Model (ODM) (CDISC ODM), a Clinical Data Interchange Standards Consortium (CDISC) Study Data Tabulation Model (SDTM) (CDISC SDTM), and/or other formats, and automatic generation of test scenarios and objective evidence of test coverage (e.g., evidence of coverage of rules/importing via automated data testing, etc.). In addition, present invention embodiments enable chaining of pre-processing tasks required for end-to-end migration (e.g., data transfer from third party systems, unzip, decrypt, derived datasets from joins of files within a file set, etc.).

Present invention embodiments provide several advantages. For example, a non-developer (e.g., with no or limited knowledge of the target database, etc.) may configure data imports for a medical clinical trial or study. Real-time feedback of the configuration may be provided to detect potential issues in data migration. Data migration may be performed from a competitor system with reduced risk/time investment. Raw clinical data may be translated to a Clinical Data Interchange Standards Consortium (CDISC) Operational Data Model (ODM) (CDISC ODM) transactional dataset, a Clinical Data Interchange Standards Consortium (CDISC) Study Data Tabulation Model (SDTM) (CDISC SDTM) transactional dataset, and/or other formats. Test scenarios documenting evidence of test execution may be generated without a need for manual testing.

An example environment for use with present invention embodiments is illustrated in FIG. 1. Specifically, the environment includes one or more server systems 110, one or more client or end-user systems 114, and one or more source systems 150. Server systems 110, client systems 114, and source systems 150 may be remote from each other and communicate over a network 112. The network may be implemented by any number of any suitable communications media (e.g., wide area network (WAN), local area network (LAN), Internet, Intranet, etc.). Alternatively, server systems 110, client systems 114, and/or source systems 150 may be local to each other in any combination, and communicate via any appropriate local communication medium (e.g., local area network (LAN), hardwire, wireless link, Intranet, etc.).

Client systems 114 enable users to interact with server systems 110 to design and manage medical clinical or other trials or studies. The server systems include a trial manager module 120 to create and manage medical clinical or other trials or studies. The trial manager module may interact with, or include, a data migration module 122 and a monitor module 124. Data migration module 122 enables performance of data migration as described below, while monitor module 124 monitors the configuration and operation of the data migration to detect and present potential issues as described below.

Database system 118 may store various information for medical clinical trials (e.g., health related or other information, patient or participant information, dosages, medical measurements, medical histories, etc.) according to the medical clinical trial data design. The database system may be implemented by any conventional or other database or storage unit, may be local to or remote from server systems 110, client systems 114, and source systems 150, and may communicate via any appropriate communication medium (e.g., local area network (LAN), wide area network (WAN), Internet, hardwire, wireless link, Intranet, etc.).

The client systems may present graphical user (e.g., GUI, etc.) or other interfaces (e.g., command line prompts, menu screens, etc.) to solicit information from users pertaining to the medical clinical trials and data migration, and may provide reports pertaining to the medical clinical trials and/or results of the data migration (e.g., errors, data validation, etc.). The client systems include various client applications 130 to interact with servers 110 and perform various actions (e.g., browser/interface software, client word processing and other applications, etc.).

Source systems 150 provide source data 140 for the medical clinical trials. This data may include various health related or other information (e.g., patient/participant information, medical histories, medical measurements or test results, etc.), and may reside within a database 128 local to or included within the source systems. The source systems may include various applications 142 to process requests to store and/or retrieve data 140 (e.g., provide retrieved data 140 preferably in the form of source files).

Server systems 110, client systems 114, and source systems 150 may be implemented by any conventional or other computer systems preferably equipped with a display or monitor, a base (e.g., including at least one hardware processor 115 (e.g., microprocessor, controller, central processing unit (CPU), etc.), one or more memories 135 and/or internal or external network interfaces or communications devices 125 (e.g., modem, network cards, etc.)), optional input devices (e.g., a keyboard, mouse or other input device), and any commercially available and custom software (e.g., server/communications software, trial manager module 120, data migration module 122, monitor module 124, client applications 130, source applications 142, browser/interface software, etc.).

Trial manager module 120, data migration module 122, and monitor module 124 may include one or more modules or units to perform the various functions of present invention embodiments described below. The various modules (e.g., trial manager module 120, data migration module 122, monitor module 124, applications 130, 142, etc.) may be implemented by any combination of any quantity of software and/or hardware modules or units, and may reside within corresponding memories 135 of the server, client, and source systems for execution by at least one corresponding processor 115.

Figure 2:
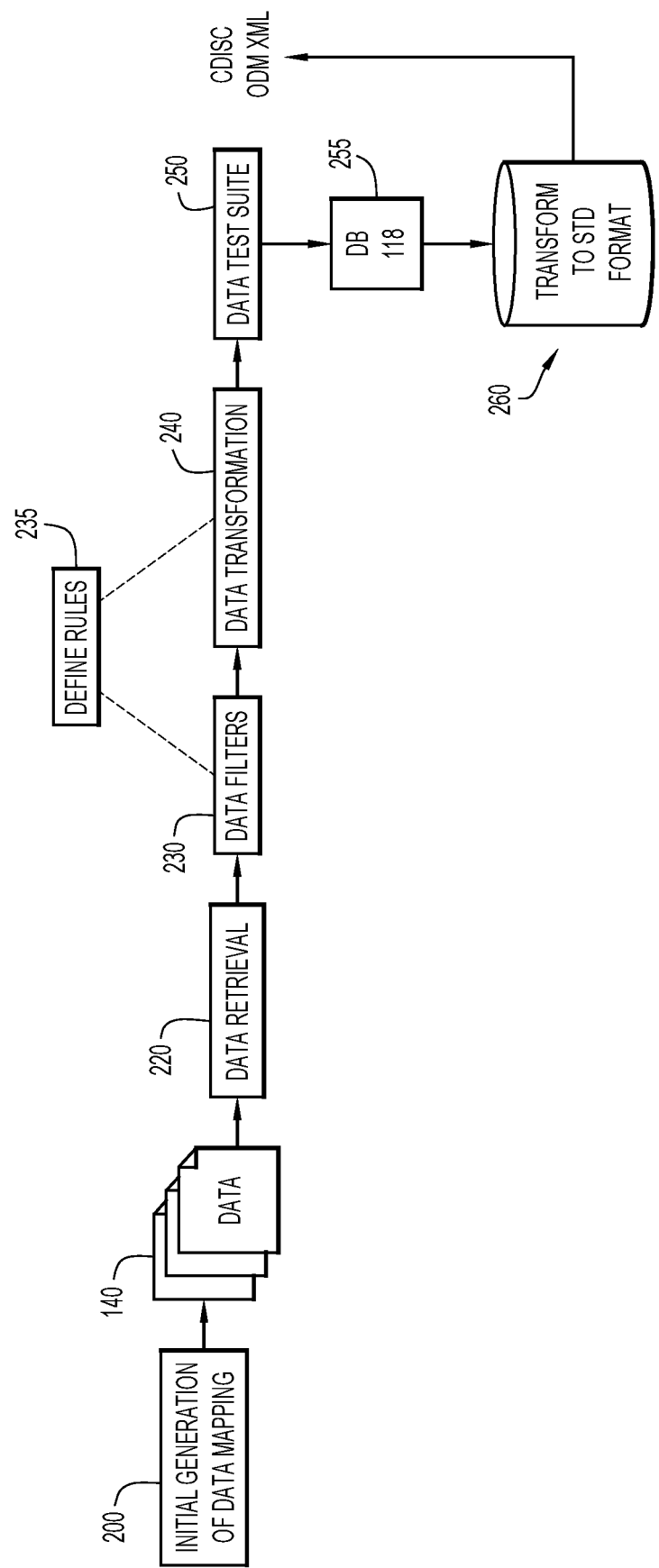
FIG. 2 is a diagrammatic illustration of migrating data from a source system to a data design or schema of a medical clinical trial or study on a target system according to an embodiment of the present invention.

A manner of migrating data from a source system to a data design or schema of a medical clinical trial or study of a target system is illustrated in FIG. 2. Initially, a user may create a medical clinical trial or study via trial manager module 120. The medical clinical trial or study preferably pertains to medical treatments and/or medications, but may pertain to any desired subject matter (e.g., psychological studies, behavioral studies, athletic performance studies, medical studies, etc.). A data design or schema is generated for the medical clinical trial to store data pertaining to the medical clinical trial. The data design or schema preferably specifies data structures and/or elements and their corresponding properties (e.g., data types, characteristics, lengths, values or value ranges, relationships between data elements, validation or other rules, etc.). For example, a user may specify (and/or select) data elements (and certain corresponding properties) and/or data structures (e.g., tables with columns/fields, etc.) to be used for the medical clinical trial. The target system handles the storage of the user-specified (and/or selected) data elements and data structures (e.g., tables, etc.) of the medical clinical trial and underlying details of the database (e.g., specific columns and properties/formats of database tables corresponding to the user-specified data elements and data structures, etc.). Thus, a user may create the data design for the medical clinical trial without knowledge of the specific details of the underlying database of the target system. Data for a medical clinical trial may be maintained in source systems 150 that typically employ a different data design or schema (e.g., based on the source database containing the data, etc.) than that used by the medical clinical trial and/or target database system.

In order to migrate data from the source systems into the data design of the medical clinical trial of the target system, mappings are defined to map the source data to data elements of the medical clinical trial data design at flow 200. This may be accomplished by a user entering the mappings, or automatically by the system based on an analysis (or comparison) of source data properties to properties of the data elements of the medical clinical trial data design. The mappings may be created and/or modified at any suitable time in the process flow. The source data elements and corresponding mapped data elements of the medical clinical trial design (and/or underlying target system database) may be in the same or different formats. Source data 140 is retrieved from source systems 150 at flow 220. Data filters and data transformations are defined to convert the source data into a form compatible with the mapped data elements of the medical clinical trial data design at flows 230, 240. This may be accomplished by a user entering the data filters and transformations, or automatically by the system based on an analysis of predetermined filters and transformations and differences between the source data and the data elements of the medical clinical trial data design. In addition, the data filters and transformations are monitored (e.g., via monitor module 124) during entry to detect and indicate potential errors or inconsistencies in the mappings in real-time at flow 235. The monitoring may detect various modifications to, and conditions, of the data migration (e.g., changes to the medical clinical trial data design, non-conforming data received from the source systems, etc.).

The filters and transformations may be tested at flow 250 to confirm that the filters and transformations are producing valid data compatible with corresponding data elements of the medical clinical trial data design. A report may be generated indicating coverage of the testing (e.g., an amount of retrieved source data correctly converted to corresponding data elements of the medical clinical trial data design, etc.). Once the filters and transformations are acceptable, data may be transformed and stored in database 118 at flow 255 (e.g., according to the mappings and medical clinical trial data design), and translated to various standard or other formats (e.g., Clinical Data Interchange Standards Consortium (CDISC) Operational Data Model (ODM) (CDISC ODM), Clinical Data Interchange Standards Consortium (CDISC) Study Data Tabulation Model (SDTM) (CDISC SDTM), etc.) for exportation to and/or processing by other applications (e.g., of the same or external systems) at flow 260. The trial manager module may perform appropriate processing (e.g., mappings, conversions, etc.) to store (and/or retrieve) the data of the medical clinical trial data design to (and/or from) the underlying database (e.g., database 118) of the target system. Thus, present invention embodiments may receive raw clinical data and provide (e.g., from the transformed state in the medical clinical trial data design) standard or other formats for use by various applications (e.g., of the same or external systems) handling data in those formats.

Figure 3:
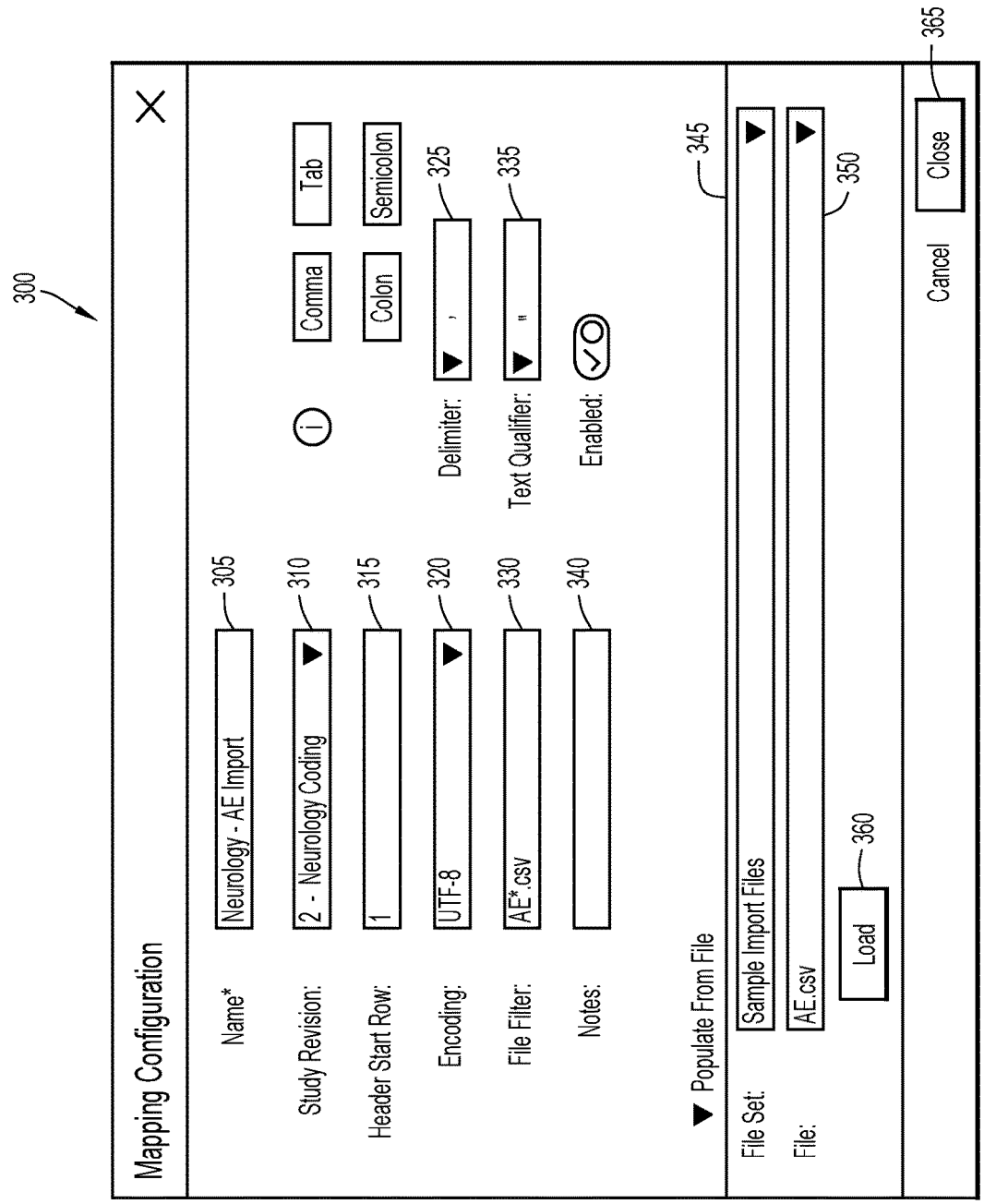
FIG. 3 is a schematic illustration of an example graphical user interface for defining properties of mappings between data elements of a source system and data elements of a data design or schema for a medical clinical trial or study on a target system according to an embodiment of the present invention.
Figure 4:
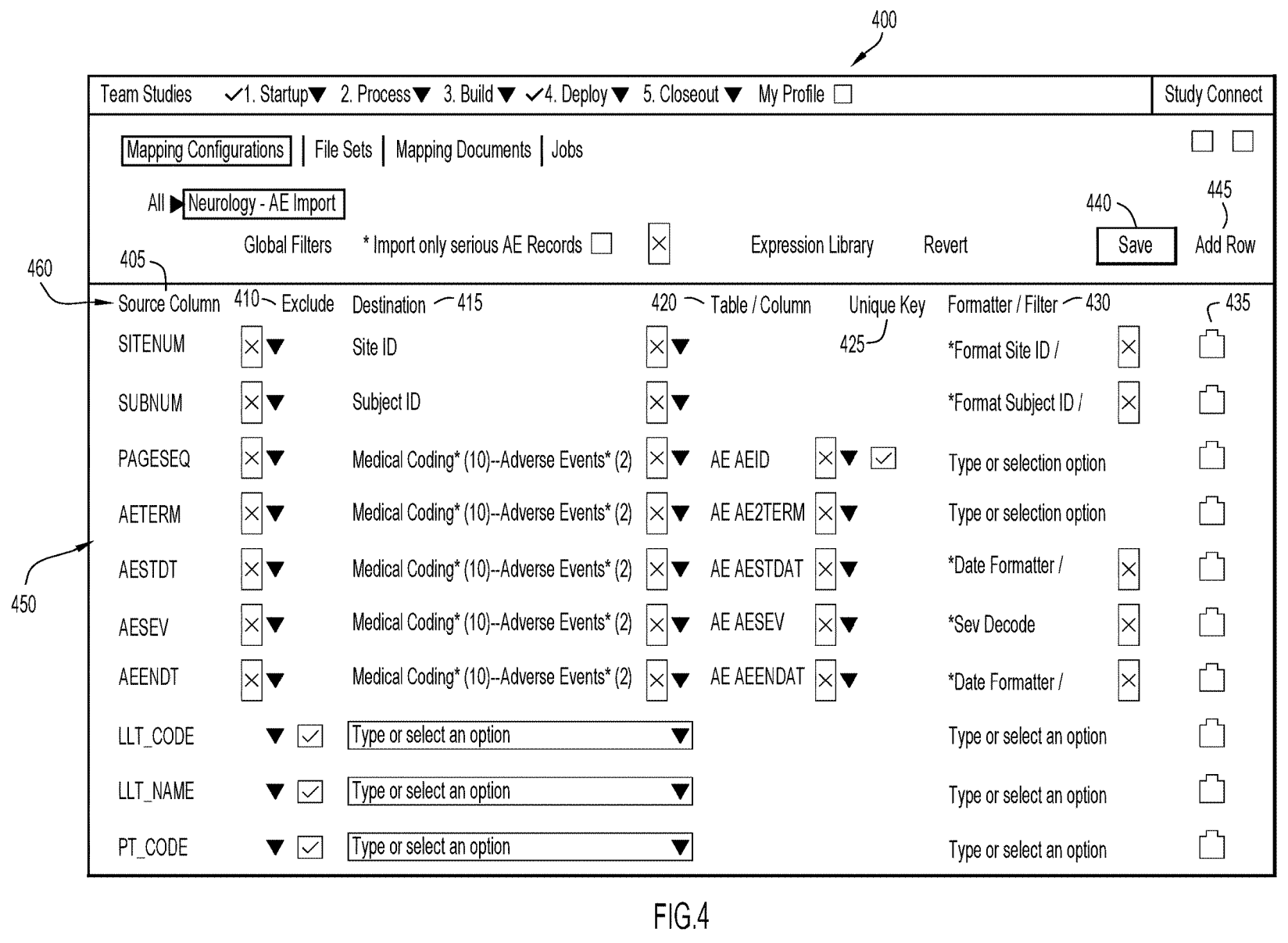

A manner of defining a mapping (e.g., via data migration module 122 and one or more server systems 110) is illustrated in FIGS. 3 and 4. Initially, a user (e.g., via a client system 114) may enter and define a mapping between source data and data elements of the medical clinical trial data design via various graphical user interfaces presented by the data migration module (e.g., corresponding to flow 200 of FIG. 2). The mappings provide a tight coupling to the target system database storing the medical clinical trial. Referring to FIG. 3, an example graphical user interface 300 enables a user to enter information into interface fields to create and indicate various properties of a mapping. By way of example, interface 300 includes: a name field 305 to specify a name of the mapping (e.g., Neurology AE-Import as viewed in FIG. 3); a study revision/version (or metadata version) field 310 (e.g., in the form of a drop-down list enabling user selection of a version of a medical study, etc.) to specify the medical clinical trial or study for which the mapping is employed (e.g., 2—Neurology Coding as viewed in FIG. 3); a header field 315 to specify a start row for a header; an encoding field 320 (e.g., in the form of a drop-down list enabling user selection of types of encoding, etc.) to specify an encoding for the data (e.g., UTF-8 as viewed in FIG. 3); a delimiter field 325 to specify a delimiter (e.g., a comma as viewed in FIG. 3); a filter file field 330 to specify a filter for the source file (e.g., AE*.csv as viewed in FIG. 3); a text qualifier field 335 to specify a text qualifier (e.g., a quotation mark as viewed in FIG. 3); and a notes field 340 to specify notes or comments pertaining to the mapping. In addition, interface 300 includes a file set field 345 (e.g., in the form of a drop-down list enabling user selection of a file set or group of source files, etc.) to specify a file set (e.g., a group of source files containing the desired source data), and a file field 350 (e.g., in the form of a drop-down list enabling user selection of a specific file, etc.) to specify the particular file within the file set for the mapping. Actuators 355, 360, and 365 on interface 300 may be respectively utilized to enable the mapping, load header data from the specified source data file (e.g., header row of a CSV file, etc.), and save the mapping.

FIG. 4 illustrates an example graphical user interface 400 utilized to enable a user to enter information in interface fields to define the data relationships of the created mapping. Interface 400 is generally in the form of a table with rows 450 defining relationships between source data and data elements of the medical clinical trial data design, and columns 460 specifying the attributes of the relationship for the mapping. By way of example, the table columns of interface 400 (e.g., with data from the header data loaded from FIG. 3, etc.) include: a source column 405 (e.g., including a drop-down list for each row enabling user selection of source data, etc.) to provide a source data element (e.g., a source database table column); an exclude column 410 (e.g., in the form of a button, etc.) to provide an indicator to identify source data excluded from the mapping; a destination column 415 (e.g., including a drop-down list for each row enabling user selection of a destination data element of the medical clinical trial data design, etc.) to provide a destination data element of the medical clinical trial data design; a target table column 420 (e.g., including a drop-down list for each row enabling user selection of a destination table of the medical clinical trial data design, etc.) to provide the table or table column in the medical clinical trial data design for the destination data element; a key column 425 (e.g., in the form of a button, etc.) to provide an indicator to identify the data element as a key field of the table in the medical clinical trial data design (and underlying target database table); and a filter column 430 (e.g., including a drop-down list for each row enabling user selection of transformations/filters, etc.) to provide the transformation/filter for converting the source data element. An actuator 435 is further included for each row to enable removing that row from the table. In addition, a save button 440 may be utilized to save the mapping definition, while an add button 445 enables adding a row to the table (e.g., to specify another relationship for the mapping).

For example, FIG. 4 illustrates relationships for the example mapping, Neurology—AE Import, specified in interface 300 of FIG. 3. The rows of interface 400 each specify a relationship or mapping between a data element from the specified source file, AE.csv, and a corresponding data element of the medical clinical trial data design (e.g., source data element/column PAGESEQ is mapped to the AE AEID table/column for a data element (or destination, Medical Coding—Adverse Events) in the medical clinical trial data design and serves as a unique key, while source data elements LLT_CODE, LLT_NAME, and PT_CODE are excluded from the mapping as viewed in FIG. 4). However, interfaces 300 and 400 may be utilized to create and define any desired mappings between source and target data. Monitor module 124 may perform real-time monitoring and error detection during creation of the mappings as described below.

Alternatively, the data migration module may automatically suggest or create and define mappings based on an analysis of the source data and properties of the data elements in the medical clinical trial data design. For example, the data migration module may compare names of data elements, corresponding data types, and/or any other properties and suggest or create a mapping between data elements having any quantity of matching (or substantially matching) properties. Further, relationships may be identified between source data and data elements in the medical clinical trial data design, and mappings may be determined based on the identified relationships. The mappings may be determined based on any quantity of any properties of the source data and data elements of the medical clinical trial data design. The suggested or created mappings may be presented and/or retrieved on interfaces 300 and/or 400 for selection, review, and/or modification by a user.

A user may create mappings prior to ascertaining complete knowledge of details of the source data. In this case, a user may initially create stub source data names and data types which can be modified at a later time, if needed, when source data and/or knowledge of the details becomes available.

Figure 5:
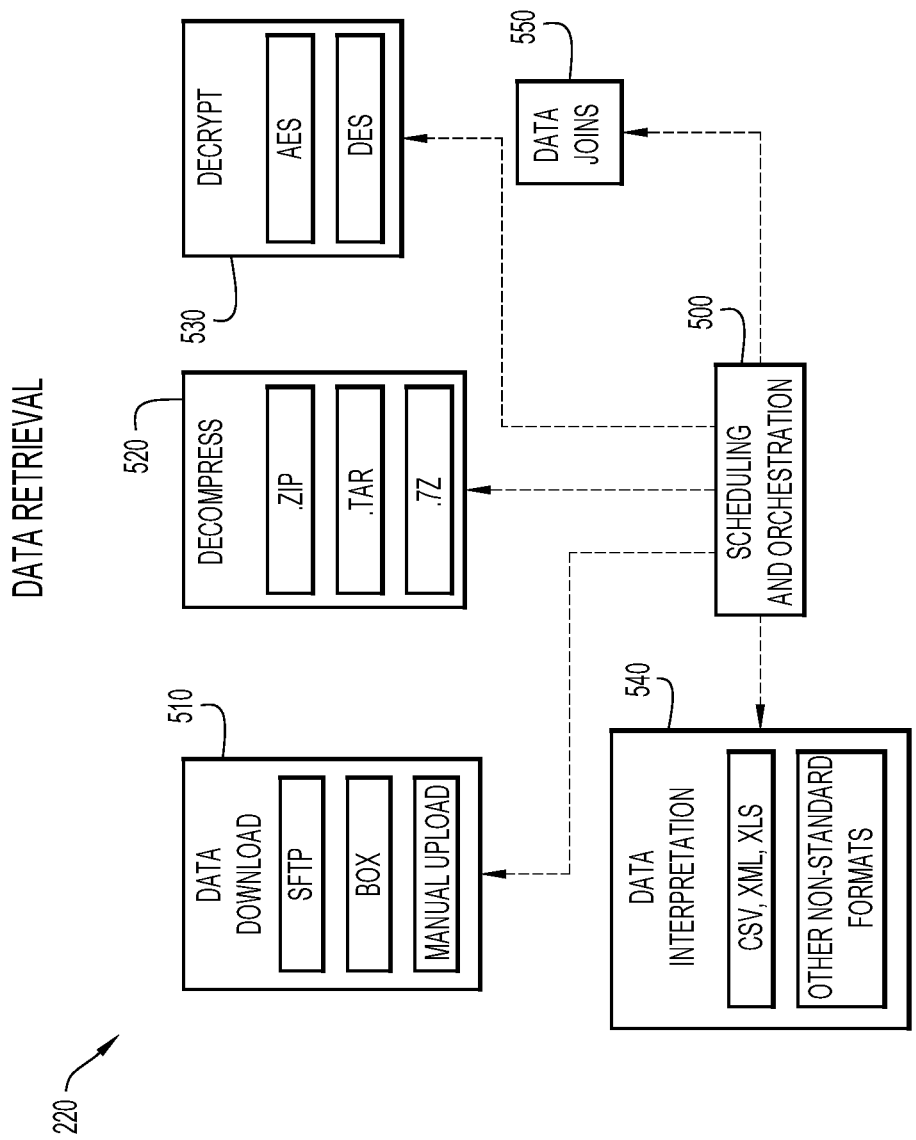
FIG. 5 is a flow diagram of a manner of retrieving data from source systems according to an embodiment of the present invention.

A manner of performing data retrieval (e.g., via data migration module 122 and one or more server systems 110) from source systems 150 is illustrated in FIG. 5. Data retrieval (e.g., corresponding to flow 220 of FIG. 2) includes building an import schedule, and retrieving and preparing source data files. Specifically, data migration module 122 includes a scheduling and orchestration module 500, a data download module 510, a decompress module 520, a decryption module 530, a data interpretation module 540, and a data join module 550.

Scheduling and orchestration module 500 controls the data retrieval process, and generates a schedule (e.g., hourly, daily, weekly, monthly, at specified times or time intervals, etc.) for importing source data from source systems 150. Scheduling and orchestration module 500 determines the appropriate modules required for data retrieval based on the source data (e.g., decompress module 520 when decompression is needed, decrypt module 530 when decryption is needed, data join module 550 to join files, etc.), and controls modules 510-550 to perform the data retrieval process. The data retrieval process may be programmable (e.g., by a user, etc.) to perform data retrieval at various times from varying source systems.

Data download module 510 configures downloads of source files from plural source systems 150. This may be accomplished via a Secure File Transfer (SFTP) or other file transfer protocol to transfer files from source systems 150, a drop-box where source files from source systems 150 have been transferred, or manual upload by the user of source files from source systems 150. Decompress module 520 decompresses the downloaded source files in the event the files have been compressed. The decompress module can accommodate various types of compressed files (e.g., .zip, .tar, .7z, etc.).

Decryption module 530 decrypts individual downloaded source files in the event the source files have been encrypted. The decryption module may accommodate various encryption schemes (e.g., Advanced Encryption Standard (AES), Data Encryption Standard (DES), etc.). Data interpretation module 540 interprets plural source file formats (e.g., CSV, XML, XMS, other non-standard formats, etc.) to enable identification of data elements within the files. The data interpretation module identifies the file type (e.g., based on the file extension or other properties, content, user-specified file types, etc.), and parses the files based on specifications for the various file formats to identify and extract data elements. Join module 550 joins data files containing overlapping, similar, and/or related data to consolidate source data files and construct a common set of records for the joined files for processing. These modules (e.g., scheduling and orchestration module 500, data download module 510, decompress module 520, decryption module 530, data interpretation module 540, data join module 550, etc.) may be arranged (or utilized) in any order to achieve a desired effect, and each may be sufficiently modular to support current and any future standards or techniques. Monitor module 124 may perform real-time monitoring and error detection during the data retrieval process as described below.

Figure 6:
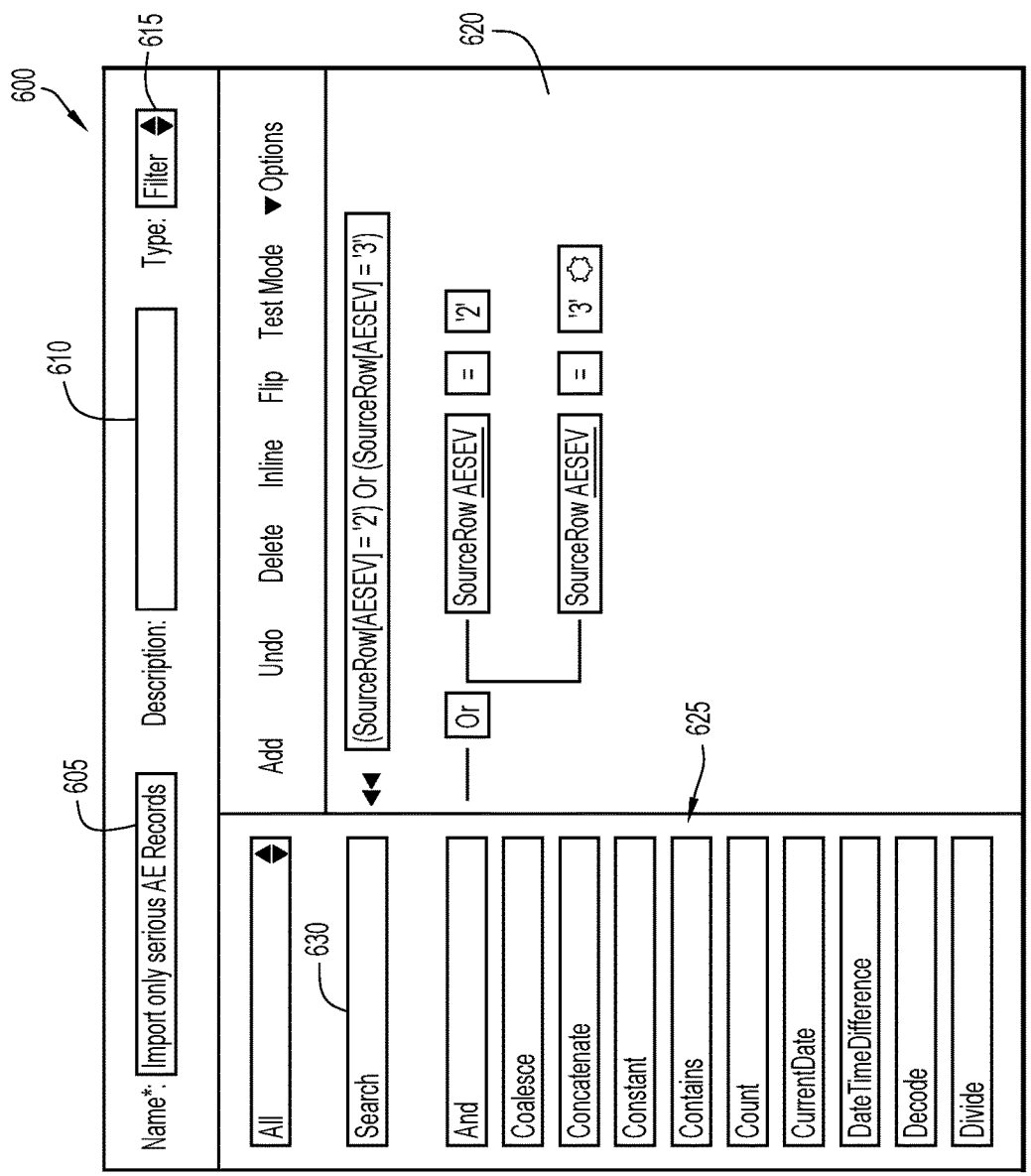
FIG. 6 is a schematic illustration of an example graphical user interface for defining filters for data migration according to an embodiment of the present invention.
Figure 7:
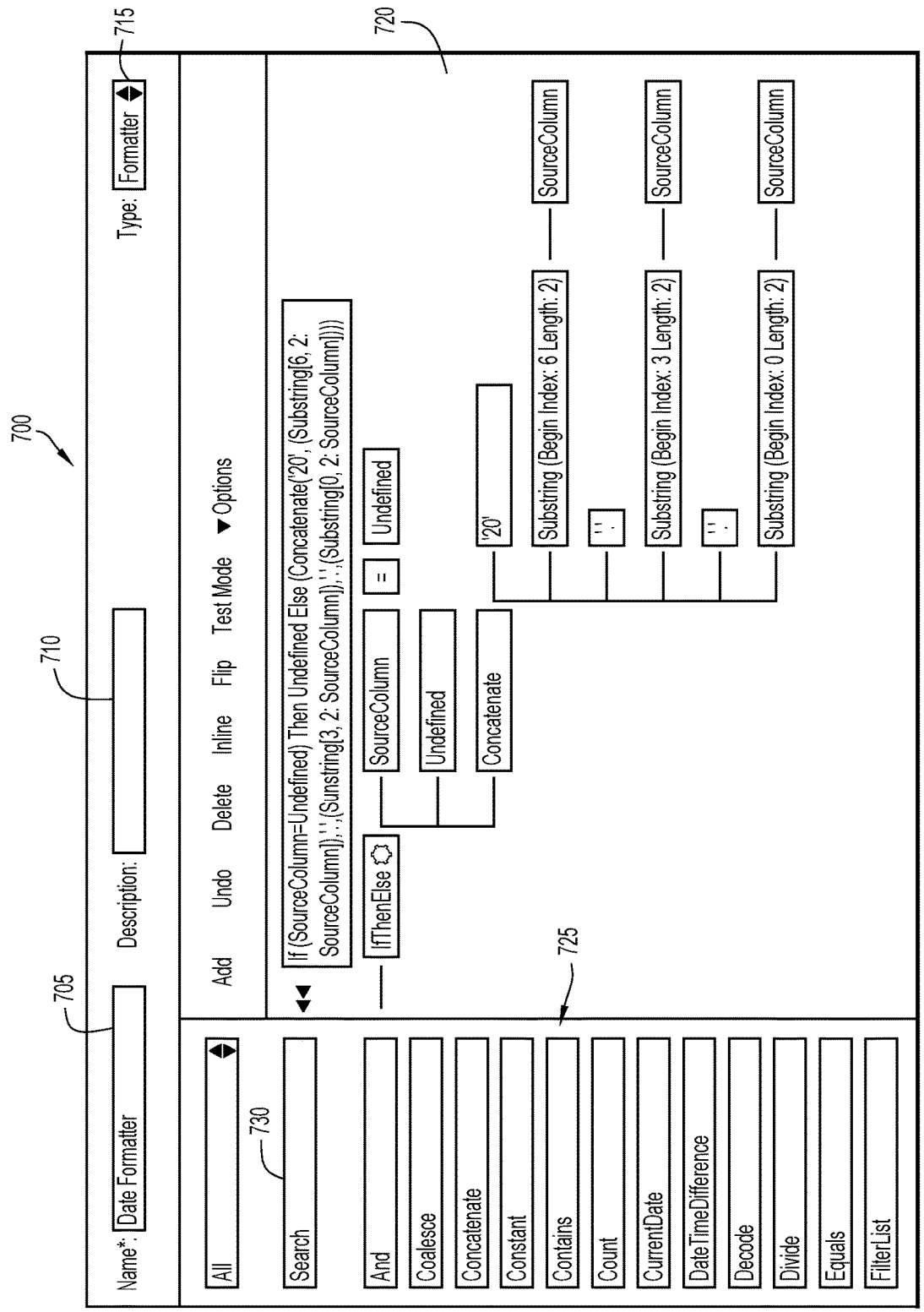
FIG. 7 is a schematic illustration of an example graphical user interface for defining data transformations for data migration according to an embodiment of the present invention.

A manner of defining filters and data transformations (e.g., via data migration module 122 and one or more server systems 110) is illustrated in FIGS. 6 and 7. Initially, a user may define filters and transformations to transform source data elements for compatibility with mapped data elements of the medical clinical trial data design via various graphical user interfaces presented by the data migration module (e.g., corresponding to flows 230 and 240 of FIG. 2). Referring to FIG. 6, an example graphical user interface 600 enables a user to enter information in interface fields to create a filter to extract certain data from source data files. Interface 600 includes: a name field 605 to specify a name of the filter (e.g., Import only serious AE Records as viewed in FIG. 6 (and as the Global Filter specified in FIG. 4)); a description field 610 to specify a description of the filter; and a type field 615 (e.g., in the form of a drop-down list enabling user selection of a transformation/filter type, etc.) to specify a type for the filter (e.g., Filter as viewed in FIG. 6). In addition, interface 600 includes an area 620 to create an expression for the filter based on selection of various operators 625 (e.g., And, Coalesce, Concatenate, etc.) and source data elements presented in the interface. A search field 630 may be used to search for specific operators and/or source data elements. By way of example, FIG. 6 illustrates the following filter expression:

(SourceRow (AESEV)='2') Or (SourceRow (AESEV='3'), where this filter extracts rows from the source data files when the source data element (or column) AESEV has a value of 2 or 3. However, any suitable filter may be defined by the user utilizing any quantity of any operators and source data elements.

FIG. 7 illustrates an example graphical user interface 700 enabling a user to enter information in interface fields to create a data transformation to transform source data to be compatible with corresponding mapped data elements of the medical clinical trial data design. Interface 700 includes: a name field 705 to specify a name of the transformation (e.g., Date Formatter as viewed in FIG. 7 (and as specified in FIG. 4); a description field 710 to specify a description of the transformation; and a type field 715 (e.g., in the form of a drop-down list to enable user selection of a transformation/filter type, etc.) to specify a type for the transformation (e.g., Formatter as viewed in FIG. 7). In addition, interface 700 includes an area 720 to create an expression for the transformation based on selection of various operators 725 (e.g., And, Coalesce, Concatenate, etc.) and source data elements presented in the interface. A search field 730 may be used to search for specific operators and/or source data elements. By way of example, FIG. 7 illustrates the following transformation expression:

If (SourceColumn=Undefined) Then Undefined
Else
(Concatenate ('20',
Substring (6, 2, SourceColumn), "."
Substring (3, 2, SourceColumn), "."
Substring (0, 2, SourceColumn))), where this transformation leaves undefined values of a column as undefined, and transforms each remaining value of the column by concatenating a string '20' with the characters at positions 6 and 7 of a column string value, a "." character, the characters at positions 3 and 4 of the column string value, a "." character, and the characters at positions 0 and 1 of the column string value. However, any suitable transformation may be defined by the user utilizing any quantity of any operators and/or source data elements. Monitor module 124 may perform real-time monitoring and error detection during creation and execution of the filters and transformations as described below.

Alternatively, the data migration module may automatically suggest or create and define filters and transformations based on an analysis of the source data and properties of the data elements in the trial data design. For example, the data migration module may compare names of data elements, corresponding data types, and/or any other properties to determine differences between the source data and data elements of the medical clinical trial data design. The differences may be used to suggest or create a filter to exclude and/or retrieve corresponding source data elements, and/or suggest or create filters and/or transformations to compensate for the differences between the source data and medical clinical trial data design (e.g., converting strings to numeric values, converting dates, etc.). For example, certain differences between the data elements may be mapped to predetermined filters and/or data transformations (e.g., missing data elements may be provided in a filter, different formats may be mapped to predefined transformations converting between formats, etc.). The filters and transformations may be determined based on any quantity of any properties of the data elements. The suggested or created filters and/or transformations may be presented and/or retrieved on interfaces 600 and/or 700 for selection, review, and/or modification by a user.

Figure 8:
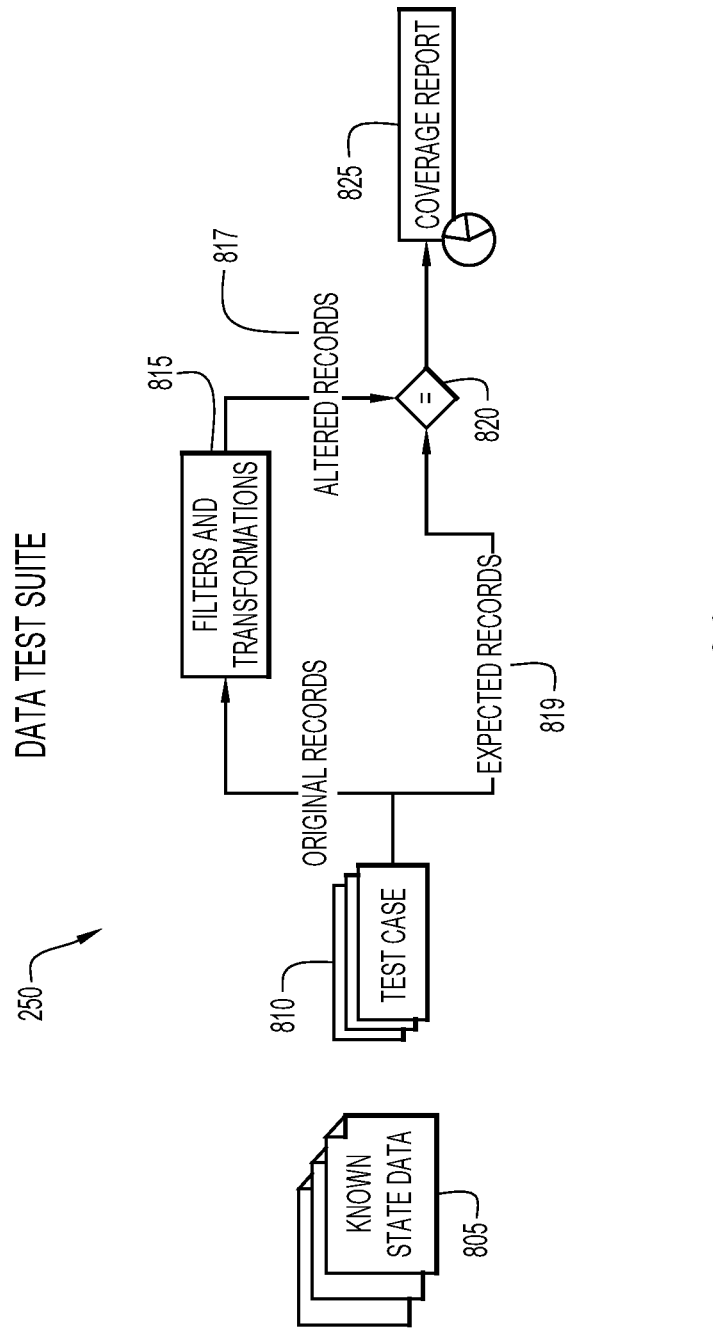
FIG. 8 is a flow diagram of a manner of testing data migration according to an embodiment of the present invention.

A manner of testing the filters and transformations (e.g., via data migration module 122 and one or more server systems 110) is illustrated in FIG. 8. The testing (e.g., corresponding to flow 250 of FIG. 2) enables automatic generation of scenario stubs (or portions of code) that, when completed (e.g., automatically or by a user), tests the various paths traversed by source data during data filter and transformation processing. Thus, a user may create test cases to verify that the filters and transformations operate as intended with the source data.

In particular, known state or test data 805 (e.g., indicating test data with known results from filter and/or transformation processing) and test cases or scenarios 810 are prepared. The test cases indicate various scenarios (e.g., indicating rules and/or conditions) for filtering and/or transforming the source data. Test data 805 is applied to test cases 810, and processed by filters and transformations at flow 815 according to the scenarios of the test cases (and test data 805) to produce altered records 817. The processing may further identify formats not used by the filters and transformations. The altered records are compared to expected records 819 for the test cases at flow 820. Each test case 810 is considered to be satisfied in response to a sufficient quantity of altered records 817 matching expected records 819 for that test case (e.g., all records matching, a specified percentage of records matching, etc.). A report 825 is generated to indicate results for test cases 810. Changes to the source and/or test data may be constantly checked to identify scenarios that have not been accounted for by that data. These scenarios may be immediately presented to a user, and/or provided in report 825.

The report may indicate the percentage coverage for all active filters and transformations to show the percentage of data-impacting rules/scenarios that have been tested (based on the test cases), and the coverage (e.g., percentage of matches between the altered and expected records) within a particular rule/scenario (e.g., for plural logic paths). This is particularly useful for clinical trial rescue studies, where data is malformed and needs to be normalized, but a customer and their sponsors need provable statistics that show their data is altered exactly according to specification.

Figure 9:
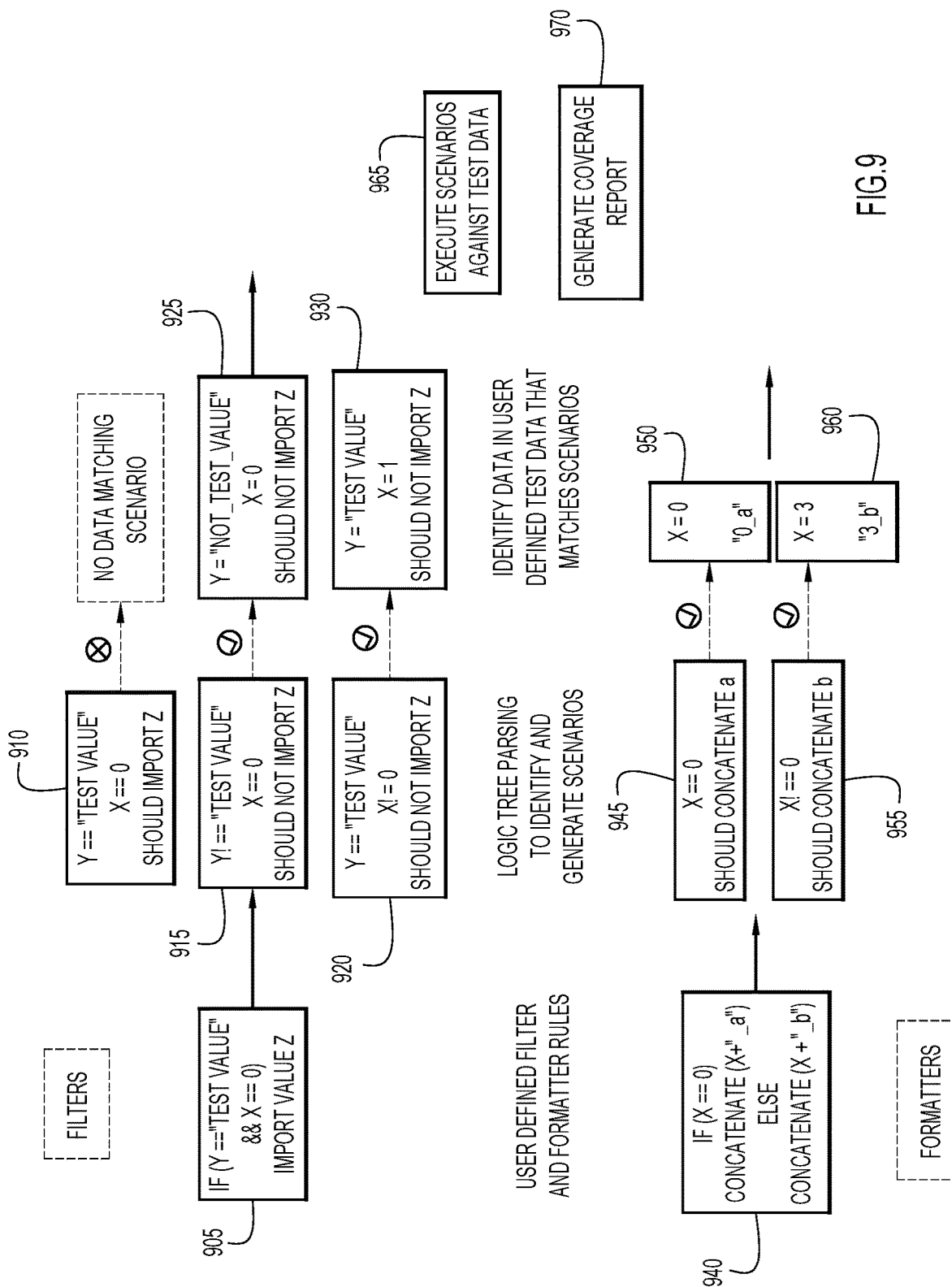
FIG. 9 is a flow diagram of examples of generating test scenarios for testing data migration according to an embodiment of the present invention.

An example manner of generating and applying test scenarios (e.g., via data migration module 122 and one or more server systems 110) is illustrated in FIG. 9. Initially, a filter 905 is selected for testing. The filter, by way of example, may be represented by the following expression:

If (Y==Test Value && X==0) Import Value Z, where the expression indicates that value Z is imported when a variable Y equals a test value and variable X equals zero.

The filter expression is parsed by the system and evaluated to determine different scenarios or paths for the source data. For example, the scenarios may include a scenario 910 where variable Y equals the test value and variable X equals zero (e.g., satisfying the rule or filter expression enabling importation of value Z), a scenario 915 where Y does not equal the test value and X equals zero (e.g., preventing importation of value Z), and a scenario 920 where variable Y equals the test value and variable X does not equal zero (e.g., preventing the importation of value Z). A stub (or portion of code) for each scenario may be generated and a user may complete the stub (e.g., specify various conditions or actions, etc.) to form a test case. Alternatively, code for the entire test case may be automatically generated by the system (e.g., based on user input or preferences, predetermined templates associated with scenarios, etc.).

Once the scenarios for the filter are determined (and/or test cases generated), source data (or source or other data designated for testing) is identified that matches each scenario. By way of example, no matching data exists for scenario 910 (e.g., data for variable Y equals a test value and data for variable X equals zero), test data 925 is identified for scenario 915 (e.g., data for variable Y does not equal the test value and data for variable X equals zero) where the value Z should not be imported, and test data 930 is identified for scenario 920 (e.g., data for variable Y equals the test value and data for variable X does not equal zero (e.g., X=1 in this example)) where the value Z should not be imported. The source data for the scenarios may be specified by the user. Alternatively, the system may determine source data for the scenarios. This may be accomplished by retrieving source data and identifying data satisfying the various scenarios. The system identifies scenarios that are unsupported by the source data (e.g., source data is lacking to satisfy conditions of a scenario), and may present the identified scenarios to the user for modification (e.g., removal, adjustment, etc.) of those scenarios for testing.

A similar process may be applied to a transformation (or formatter). Initially, a transformation or formatter 940 is selected for testing. The formatter, by way of example, may be represented by the following expression:

If (X==0)
   Concatenate (X+"_a")
Else
   Concatenate (X+"_b"), where the expression indicates that the variable X is concatenated with the string "_a" when the variable X equals a zero character ("0"), and the variable X is concatenated with the string "_b" when the variable X does not equal the zero character.

The transformation expression is parsed by the system and evaluated to determine different scenarios or paths for the source data. For example, the scenarios may include a scenario 945 where variable X equals the zero character and should be concatenated with the string "_a", and a scenario 955 where variable X does not equal the zero character and should be concatenated with the string "_b". A stub (or portion of code) for each scenario may be generated and a user may complete the stub (e.g., specify various conditions or actions, etc.) to form a test case. Alternatively, code for the entire test case may be automatically generated by the system (e.g., based on user input or preferences, predetermined templates associated with scenarios, etc.).

Once the scenarios for the transformation are determined (and/or test cases generated), source data (or source or other data designated for testing) is identified that matches each scenario. By way of example, test data 950 is identified for scenario 945 (e.g., data for variable X equals the zero character and should be concatenated with the string "_a" to yield a new string of "0_a"), and test data 960 is identified for scenario 955 (e.g., data for variable X does not equal the zero character and should be concatenated with the string "_b" (e.g., a data value for the variable X of '3' should yield a resulting string of "3_b")). The source data for the scenarios may be specified by the user. Alternatively, the system may determine source data for the scenarios. This may be accomplished by retrieving source data and identifying data satisfying the various scenarios. The system identifies scenarios that are unsupported by the source data (e.g., source data is lacking to satisfy conditions of a scenario), and may present the identified scenarios to the user for modification (e.g., removal, adjustment, etc.) of those scenarios for testing.

The test cases for the scenarios may be executed against the corresponding identified test data at flow 965, and a coverage report may be generated at flow 970 providing results of the test cases in substantially the same manner described above (e.g., FIG. 8).

Figure 10:
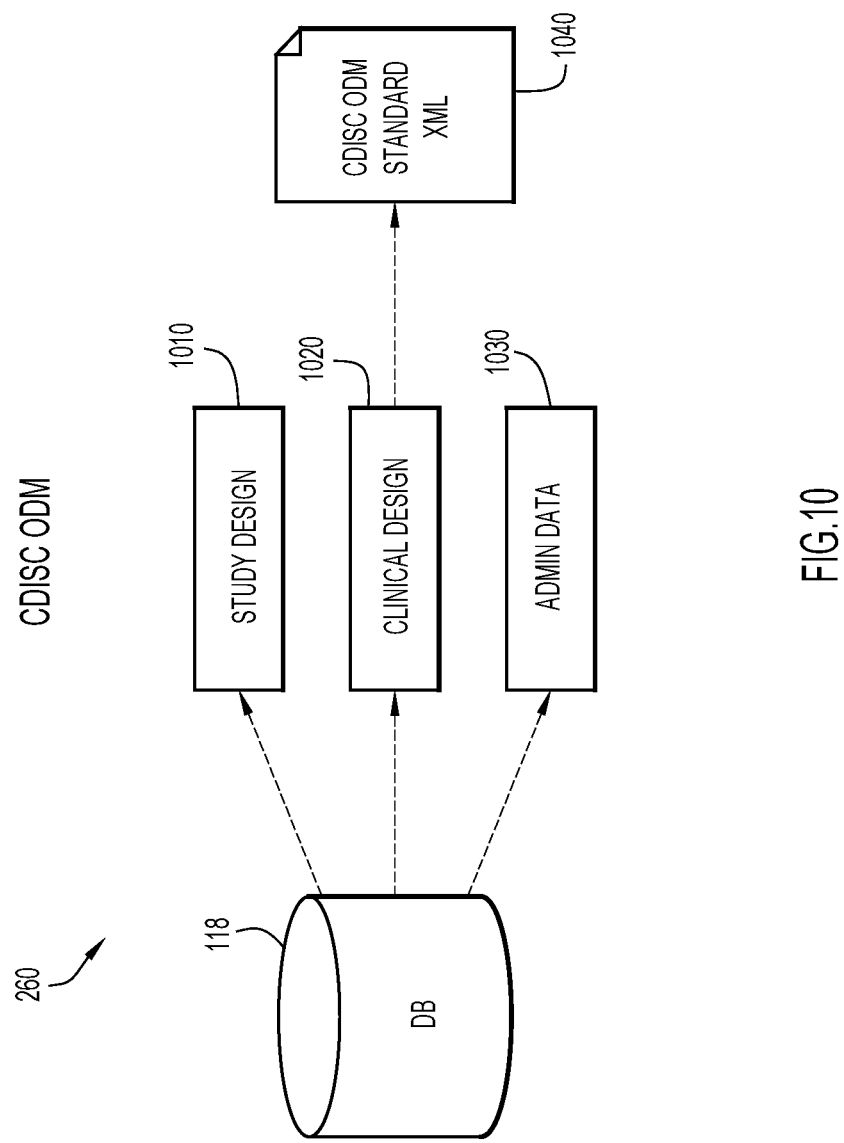
FIG. 10 is a flow diagram of a manner of transforming data of a target system to a desired format according to an embodiment of the present invention.

A manner of exporting the transformed data of the medical clinical trial data design in various standard or other formats (e.g., via data migration module 122 and one or more server systems 110) is illustrated in FIG. 10. Since source data is already mapped to data elements of a medical clinical trial data design as described above, the transformed data may be exported (e.g., corresponding to flow 260 of FIG. 2) in various standard or other formats (e.g., Clinical Data Interchange Standards Consortium (CDISC) Operational Data Model (ODM) formatted XML (CDISC ODM), Clinical Data Interchange Standards Consortium (CDISC) Study Data Tabulation Model (SDTM) formatted XML (CDISC SDTM), etc.). By way of example, data for Clinical Data Interchange Standards Consortium (CDISC) Operational Data Model (ODM) includes study design data 1010 (e.g., data pertaining to the medical clinical trial data design), clinical data 1020 (e.g., health-related, patient/participant, or other data of the medical clinical trial retrieved from source systems 150), and administrative data 1030 (e.g., data relating to administering the medical clinical trial, user information, location information, etc.). Study design data 1010 and administrative data 1030 pertain to the medical clinical trial and are stored by the target system (e.g., database 118) in response to creation and/or implementation of the medical clinical trial data design. Clinical data 1020 corresponds to the data for the medical clinical trial from source data of source systems 150. This data is processed and transformed to be stored in database 118 according to the medical clinical trial data design as described above.

The various data components 1010, 1020, and/or 1030 are assembled and converted to a desired format (e.g., Clinical Data Interchange Standards Consortium (CDISC) Operational Data Model (ODM) formatted XML, etc.), and exported as one or more files 1040 of the desired format for use by third party or other data consumers. The conversion may be performed by arranging and/or adjusting data 1010, 1020, and 1030 in accordance with a specification for data elements of the desired formats. The specification may provide rules for the format, syntax, and other format properties (e.g., data types, file and/or data arrangements, delimiters, section headers, etc.). By combining the import capabilities and medical clinical trial management of present invention embodiments, raw clinical or other data may be transformed into standard or other formats which may be used for submission to, or consumption by, third party systems. Thus, present invention embodiments provide real-time checking of the data migration with transformation and exportation of raw clinical data (e.g., transformed to the medical clinical trial data design) in desired standard or other formats.

Monitor module 124 (e.g., via one or more server systems 110) monitors various aspects of the data migration. For example, monitor module 124 may monitor transactions or jobs performed for the data migration and provide transaction or job status. FIG. 11 illustrates an example graphical user interface 1100 utilized to monitor and provide status information for transactions or jobs of the data migration. Interface 1100 is generally in the form of a table with a row for each transaction, and columns 1160 specifying attributes of the transaction. By way of example, the table columns of interface 1100 include: an output set column 1105 providing the output set for a transaction; a type column 1110 providing a type of the transaction (e.g., import, etc.); a status column 1115 providing a status for a transaction (e.g., complete, failed, etc.); a date/time column 1120 providing a start time for a transaction; a requester column 1125 indicating a user requesting the transaction; a processed status column 1130 providing a quantity of data files processed; a log column 1135 providing a link to a log file for the transaction; and an actions column 1140 providing actions for the transaction. The monitor module may determine status of transactions periodically or at any specified times or time intervals. The status information may be retrieved based on queries to one or more server systems 110 performing the transactions and maintaining statistics or other information pertaining to the processing.

Figure 12:
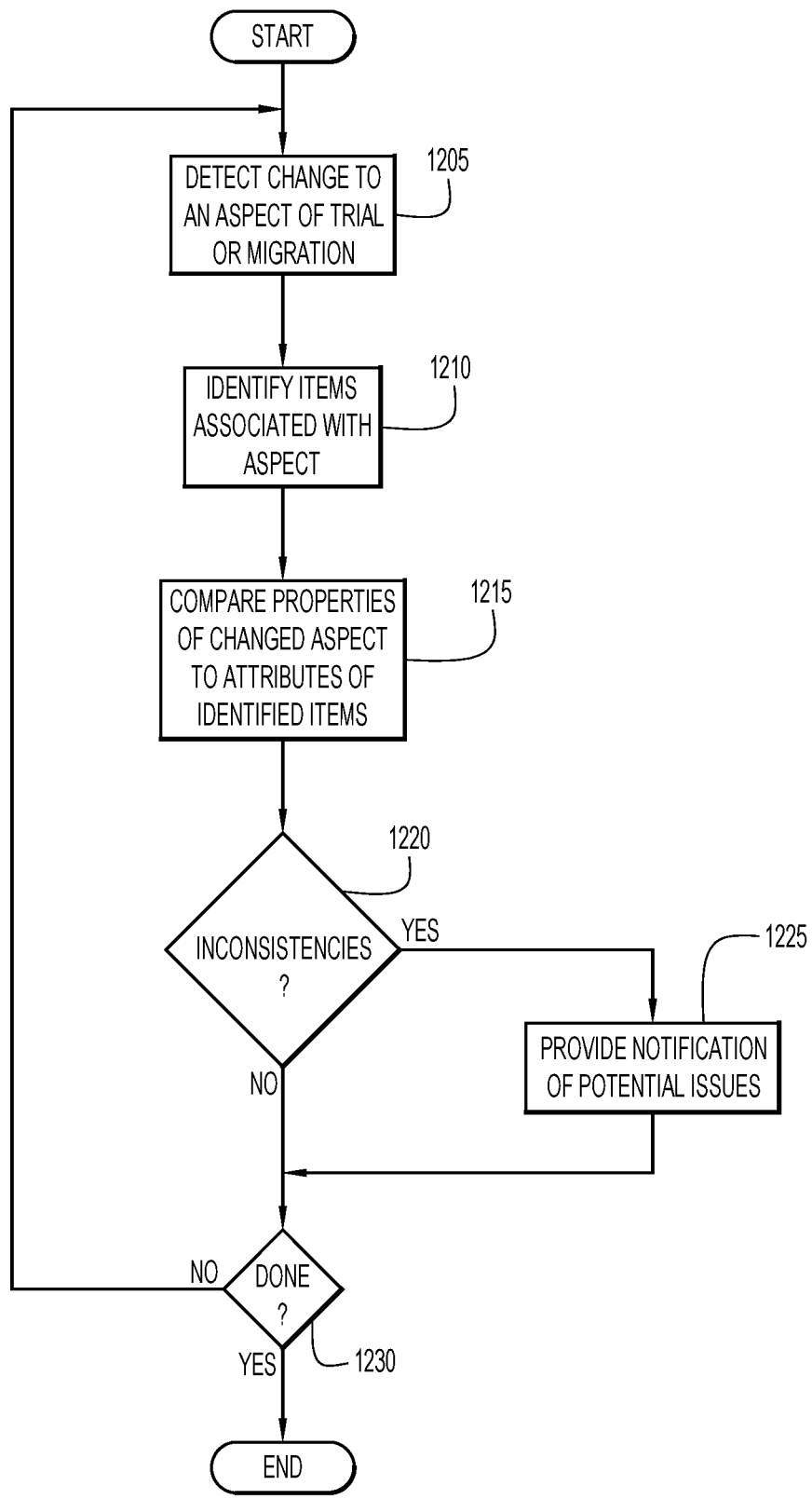
FIG. 12 is a procedural flowchart illustrating a manner of detecting potential issues for data migration in real-time according to an embodiment of the present invention.

Monitor module 124 (e.g., via one or more server systems 110) may further monitor changes to data and/or the medical clinical trial data design and determine potential issues resulting from those changes in real-time (e.g., corresponding to flow 235 of FIG. 2). A manner of detecting potential issues in real-time (e.g., via monitor module 124 and one or more server systems 110) is illustrated in FIG. 12. Specifically, a user may change a mapping, data elements of the medical clinical trial data design, or other aspects of the data migration or medical clinical trial data design, and the change is detected at step 1205. The monitor module may be constantly detecting changes in real-time during interaction with (e.g., via graphical user interfaces 300, 400, 600, and/or 700, etc.) or processing by migration module 122. For example, the monitor module may detect changes during accessing or interaction with an interface, retrieval of source data, modifications to mappings, filters, and/or transformations, etc. Potential configuration or other issues are presented to a user in real-time (e.g., via an interface presented with (or overlaid on) any interface with which a user may be interacting, etc.). A user may navigate from the presented interface providing the detected issues (e.g., including a link or other navigation actuator, etc.) to an appropriate interface to address the identified issue.

The particular data elements of the source data and/or medical clinical trial data design affected by the changed aspect are determined, and associated items (e.g., mappings, data elements of the medical clinical trial data design, transformations, filters, etc.) impacting or including the determined elements are identified at step 1210.

Properties of the changed aspect are compared to attributes of the associated item to determine inconsistencies indicating potential issues or configuration errors for the data migration. The potential issues may include invalid mappings, filters, and/or transformations due to changes in aspects of the data migration. For example, a deleted data element of the medical clinical trial design may render corresponding mappings, transformations, and/or filters invalid, a changed data type may render corresponding mappings, transformations, and/or filters invalid, a modified operation of a filter or transformation may be inconsistent with data types of the corresponding data elements of the source systems and/or medical clinical trial data design, etc. The inconsistencies may further be detected based on feedback from job execution (e.g., an import failure for source data, etc.). In this case, a log may be maintained of errors encountered during job execution.

When an inconsistency or potential error is identified at step 1220, a notification including a description of the potential error is provided at step 1225. The notification (e.g., indicating potential configuration or other issues, etc.) is presented to a user in real-time (e.g., via an interface presented with (or overlaid on) any interface with which a user may be interacting, etc.). A user may navigate from the presented interface providing the detected issues (e.g., including a link or other navigation actuator, etc.) to an appropriate interface to address the identified issue. Alternatively, the system may automatically suggest or perform modifications based on the identified issue (e.g., suggest or correct data types for data elements of mappings, filters, and/or transformations, suggest or modify source or medical clinical trial data design elements for mappings, filters, and/or transformations, suggest or modify operators for filters and/or transformations, etc.). In addition, transactions or jobs associated with the identified issues and executing may be terminated or suspended depending upon the severity of the issue (e.g., transactions or jobs may be terminated or suspended for critical errors, etc.).

The process continues until termination or power down of the system as determined at step 1230. The identification of potential issues preferably occurs in real-time. For example, a user may enter changes and potential issues are identified during entry of the changes. Alternatively, the potential issues may be identified when changes are instructed to be committed. A notification may be presented informing a user of potential issues or errors prior to committing the change. The notification may also prompt a user for confirmation to commit the changes.

Figure 13:
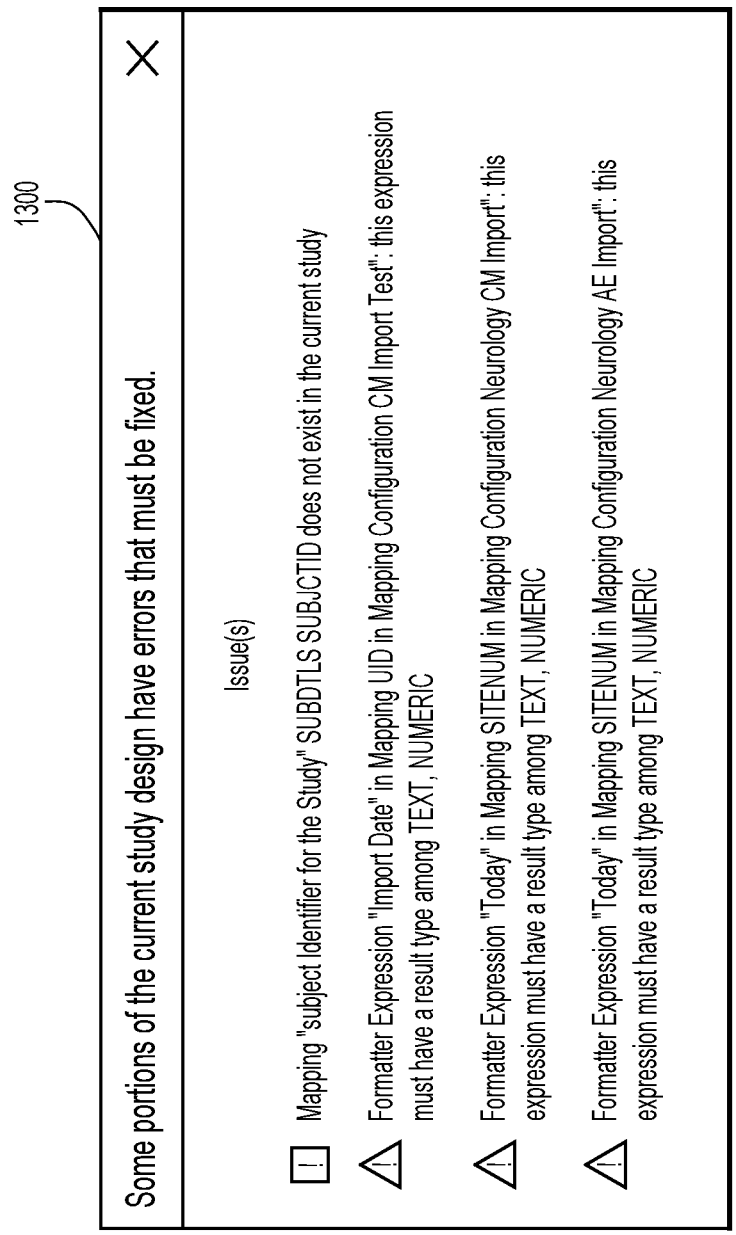
FIG. 13 is a schematic illustration of an example graphical user interface for real-time feedback of potential issues for data migration according to an embodiment of the present invention.

An example graphical user interface 1300 presenting a description of potential issues or errors is illustrated in FIG. 13. In particular, interface 1300 is presented in response to real-time identification of potential issues or errors arising from changes to aspects of the data migration or medical clinical trial data design. By way of example, interface 1300 specifies each individual potential issue or error for a change, and a description of the error. These errors may include non-existent data elements in the medical clinical trial data design, and inconsistent data types (e.g., text or numeric data types required, etc.) in a transformation (filter or formatter) (e.g., as shown in FIG. 13).

Interface 1300 may be presented at various times. For example, the interface may be presented in response to identification of potential issues during entry of the changes. Alternatively, the interface may be presented in response to identification of potential issues, and/or when an individual instructs a change to be committed. The interface may be presented informing a user of potential issues or errors prior to committing the change, and may also include an actuator to prompt a user for confirmation to commit the changes despite the potential issues or errors. Interface 1300 may be presented with (or overlaid on) any interface with which a user may be interacting. In addition, the interface may include a link or other navigation actuator to enable a user to navigate from the presented interface to an appropriate interface to address the identified issue (e.g., interface 400 to modify a mapping, etc.).

Figure 14:
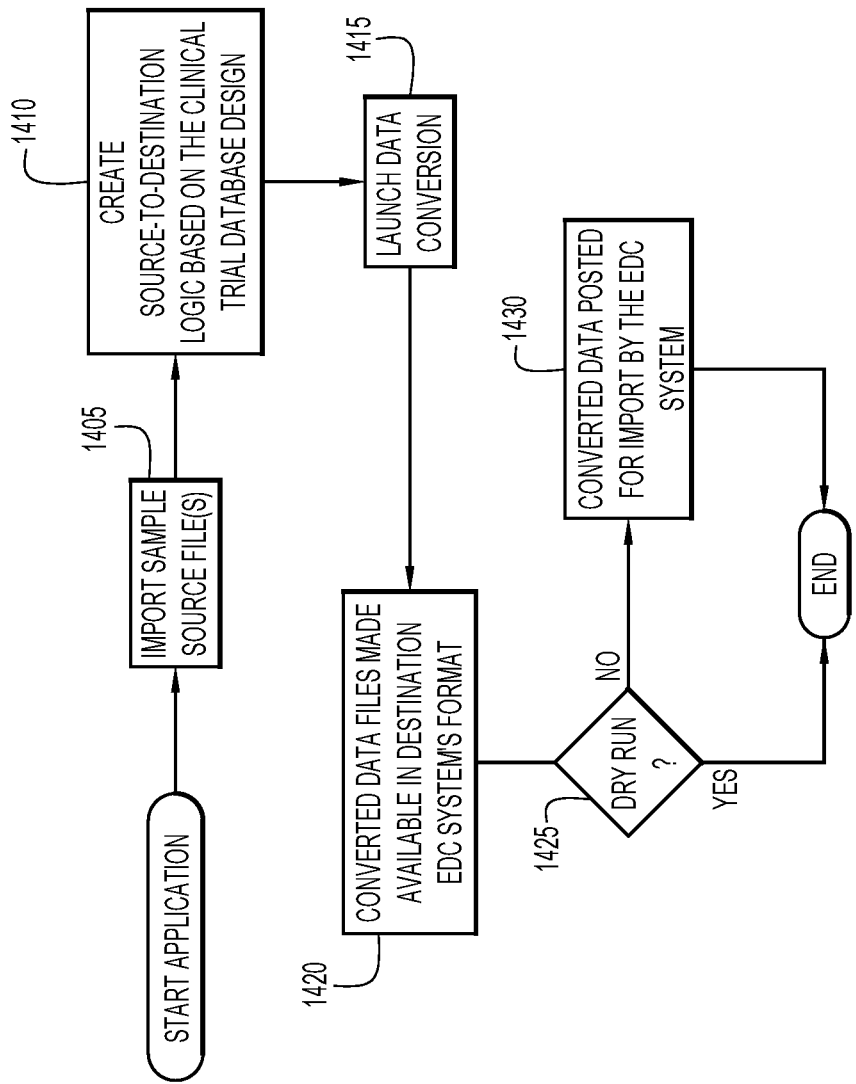
FIG. 14 is a procedural flowchart illustrating a manner of migrating data between a source system and a data design or schema of a medical clinical trial or study of a target system according to an embodiment of the present invention.

A manner of performing data migration (e.g., via data migration module 122 and one or more server systems 110) according to an embodiment of the present invention is illustrated in FIG. 14. Initially, a user requests performance of data migration by one or more server systems 110 from a client system 114. The user may specify source systems 150 storing desired data to be migrated. Source files from the specified source systems are imported and processed (e.g., identify file types and formats to identify data elements, decompression, decryption, etc.) at step 1405 (e.g., corresponding to flow 220 of FIG. 2). Mappings (and filters and/or transformations) to transfer the source data to corresponding data elements of the medical clinical trial data design may be created at step 1410 (or at other suitable times in the process flow) via user interfaces or automatically by the system (e.g., corresponding to flow 200 of FIG. 2).

The source data is transformed to the format of the corresponding data elements of the medical clinical trial data design at step 1415 based on the mappings, filters, and transformations, and the converted data files are made available in the appropriate format for an electronic data capture component (EDC) of the target system at step 1420 (e.g., corresponding to flows 230, 240 of FIG. 2). A dry run may be requested where the data is processed for conversion, but not imported into the target system. This provides an opportunity to debug the data migration (e.g., corresponding to flow 250 of FIG. 2) prior to storing the source data in the medical clinical data design of the target system. If a dry run is requested as determined at step 1425, the data is processed (but not imported) and inspected. The resulting data may be tested as described above and corrective actions performed, if needed.

When a dry run is not requested, the data is processed for conversion and imported into the mapped data elements of the medical clinical trial data design of the target system (e.g., corresponding to flow 255 of FIG. 2) at step 1430. Monitor module 124 may perform real-time monitoring and error detection during the data migration as described above.

It will be appreciated that the embodiments described above and illustrated in the drawings represent only a few of the many ways of implementing embodiments for data migration from a source system to a data schema of a medical study on a target system.

The environment of the present invention embodiments may include any number of computer or other processing systems (e.g., client or end-user systems, server systems, source systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, trial manager module, data migration module, monitor module, etc.). These systems may include any types of monitors and input devices (e.g., keyboard, mouse, voice recognition, etc.) to enter and/or view information.

It is to be understood that the software (e.g., trial manager module, data migration module, monitor module, etc.) of the present invention embodiments may be implemented in any desired computer language and could be developed by one of ordinary skill in the computer arts based on the functional descriptions contained in the specification and flow charts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client, source, and server systems, and/or any other intermediary processing devices. The software and/or algorithms described above and illustrated in the flow charts or diagrams may be modified in any manner that accomplishes the functions described herein. In addition, the functions in the flow charts, diagrams, or description may be performed in any order that accomplishes a desired operation.

The software of the present invention embodiments (e.g., trial manager module, data migration module, monitor module, etc.) may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information (e.g., source data, mappings, medical clinical trial data, reports, etc.). The database system may be implemented by any number of any conventional or other databases, data stores or storage structures (e.g., files, databases, data structures, data or other repositories, etc.) to store information (e.g., source data, mappings, medical clinical trial data, reports, etc.). The database system may be included within or coupled to the server, client, and/or source systems. The database systems and/or storage structures may be remote from or local to the computer or other processing systems, and may store any desired data (e.g., source data, mappings, medical clinical trial data, reports, etc.).

The present invention embodiments may employ any number of any type of user interface (e.g., Graphical User Interface (GUI), command-line, prompt, etc.) for obtaining or providing information (e.g., migration requests, test cases, test data, reports, mappings, filters, transformations, issues or errors, etc.)), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interfaces may include any suitable actuators (e.g., links, tabs, etc.) to navigate between the screens in any fashion.

The report may include any information arranged in any fashion, and may be configurable based on rules or other criteria to provide desired information to a user (e.g., test scenarios/cases, test coverage, pass/fail rates, etc.).

The present invention embodiments are not limited to the specific tasks or algorithms described above, but may be utilized for data migration between any schemas of source and target systems. The trial data design may include any quantity of any types of data structures (e.g., tables, etc.) and data elements (e.g., fields, etc.) arranged in any fashion. The data structures and data elements may have any desired properties (e.g., dimensions, data or other types, lengths, formats, etc.). The trial or study may pertain to any desired subject matter (e.g., medical treatments and/or medications, psychological studies, behavioral studies, athletic performance studies, medical studies, food studies, etc.). The trial data design may include any desired data structures and elements in formats that may be the same or different than the format of the underlying database of the target system.

The source system may store any data (e.g., health-related, trial-related, patient/trial participant, etc.) in any desired data structures (e.g., tables, files, etc.) and in any desired formats that may be the same or different than the formats of the data design of the trial and/or underlying database of the target system. The data retrieval process may retrieve any data from the source systems in any format (e.g., individual data elements, files, compressed, uncompressed, encrypted, decrypted, etc.), and may be performed at any specified times or periodically at any desired time intervals. The mappings may map any quantity of any types of source elements from any data structures to any quantity of any desired data elements of the trial data design (e.g., one-to-one mapping, one-to-many mappings, data elements of the same or different types or formats, etc.). The filters and transformations may include any quantity of operators and data elements to perform any suitable filtering and/or transformations. The filters and transformations may include any types of expressions (e.g., mathematical, logical, string/character manipulation, etc.).

The test cases may be generated by a user or automatically. The system may create any portion of the test stubs to detect conditions and perform any desired actions. The testing may be initiated by a user, or by the system (e.g., at specified times or time intervals, in response to detection of an issue or error, etc.). The testing may be optional and/or performed at any desired intervals (e.g., at specified times, periodically at time intervals, at certain points in the migration process, after creation of one or more filters and/or transformations, etc.). The trial data may be exported in any desired format (e.g., standard or non-standard formats, formats expected by applications for processing, etc.) to effectively convert raw clinical or other data to the desired format.

The data migration may be monitored in real-time (e.g., during management of the trial, entry of mappings, filters, and/or transformations, etc.) to detect any types of errors and notify a user (e.g., configuration errors, data errors (e.g., inconsistent data types, etc.), execution errors or failures, errors encountered from testing, etc.). An interface may be presented upon detection of the errors to present errors to a user. The interface may be displayed separately from, or overlaid upon, any interface currently engaged by the user. The interface may enable a user to navigate to other interfaces to address the issues. Alternatively, the system may suggest or implement corrections to resolve the errors. The data migration process may be performed in response to a user request, and/or at any desired time intervals (e.g., specified times, periodically at specified time intervals, after retrieval of data from one or more source systems, etc.).

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method of migrating data between source and target systems comprising:
   retrieving data from one or more source systems;
   mapping the retrieved data from the one or more source systems to corresponding data elements of a data design for a computer implemented scenario on the target system, wherein the data elements of the data design have corresponding data types and a specification indicates storage of the data elements of the data design in associated database objects of the target system, and wherein one or more of the data elements of the data design are stored in the database objects on the target system having a data type different than a data type of the one or more data elements in the data design;

generating filters and transformations based on the mapping and data design and converting the retrieved data of the one or more source systems to the data types of the corresponding data elements of the data design based on the generated filters and transformations;

adjusting one or more from a group of the mapping, filters, and transformations in response to detecting at least one from a group of modifications to the data design and non-conforming data received from the one or more source systems;

storing the converted data for the corresponding data elements on the target system by transforming the corresponding data elements of the data design to data types of the database objects of the target system; and retrieving information from the database objects of the target system for use by the computer implemented scenario by accessing the data elements of the data design associated with the database objects.

2. The method of claim 1, further comprising:
generating and executing test cases to verify the generated filters and transformations and determine an amount of the retrieved data correctly converted for the corresponding data elements of the data design in the target system.

3. The method of claim 1, further comprising:
transforming the data elements of the data design in the target system to a standard format used by one or more external systems and exporting the transformed data to the one or more external systems for processing.

4. The method of claim 3, wherein the standard format includes one or more from a group of Clinical Data Interchange Standards Consortium Operational Data Model (CDISC ODM) and Clinical Data Interchange Standards Consortium Study Data Tabulation Model (CDISC SDTM).

5. The method of claim 1, wherein mapping the retrieved data comprises:
mapping the retrieved data from the one or more source systems to the corresponding data elements of the data design for the computer implemented scenario via a user interface.

6. The method of claim 5, wherein the mapping is independent of formats of the retrieved data and for storing the corresponding data elements on the target system.

7. The method of claim 1, wherein the computer implemented scenario includes a medical clinical trial.

8. The method of claim 1, further comprising:
detecting the modifications to the data design and the non-conforming data received from the one or more source systems in real-time; and
providing notifications of errors due to the detected modifications and non-conforming data.

9. A computer program product for migrating data between source and target systems, the computer program product comprising a computer readable storage medium having program instructions embodied therewith, the program instructions executable by a processor to cause the processor to:
retrieve data from one or more source systems;
map the retrieved data from the one or more source systems to corresponding data elements of a data design for a computer implemented scenario on the target system, wherein the data elements of the data design have corresponding data types and a specification indicates storage of the data elements of the data design in associated database objects of the target system, and wherein one or more of the data elements of the data design are stored in the database objects on the target system having a data type different than a data type of the one or more data elements in the data design;

generate filters and transformations based on the mapping and data design and convert the retrieved data of the one or more source systems to the data types of the corresponding data elements of the data design based on the generated filters and transformations;

adjust one or more from a group of the mapping, filters, and transformations in response to detecting at least one from a group of modifications to the data design and non-conforming data received from the one or more source systems;

store the converted data for the corresponding data elements on the target system by transforming the corresponding data elements of the data design to data types of the database objects of the target system; and retrieve information from the database objects of the target system for use by the computer implemented scenario by accessing the data elements of the data design associated with the database objects.

10. The computer program product of claim 9, wherein the program instructions are further configured to cause the processor to:
generate and execute test cases to verify the generated filters and transformations and determine an amount of the retrieved data correctly converted for the corresponding data elements of the data design in the target system.

11. The computer program product of claim 9, wherein the program instructions are further configured to cause the processor to:
transform the data elements of the data design in the target system to a standard format used by one or more external systems and export the transformed data to the one or more external systems for processing.

12. The computer program product of claim 11, wherein the standard format includes one or more from a group of Clinical Data Interchange Standards Consortium Operational Data Model (CDISC ODM) and Clinical Data Interchange Standards Consortium Study Data Tabulation Model (CDISC SDTM).

13. The computer program product of claim 9, wherein mapping the retrieved data comprises:
mapping the retrieved data from the one or more source systems to the corresponding data elements of the data design for the computer implemented scenario via a user interface.

14. The computer program product of claim 13, wherein the mapping is independent of formats of the retrieved data and for storing the corresponding data elements on the target system.

15. The computer program product of claim 9, wherein the computer implemented scenario includes a medical clinical trial.

16. The computer program product of claim 9, wherein the program instructions are further configured to cause the processor to:
detect the modifications to the data design and the non-conforming data received from the one or more source systems in real-time; and
provide notifications of errors due to the detected modifications and non-conforming data.

17. A system for migrating data between source and target systems comprising:
at least one processor configured to:
retrieve data from one or more source systems;
map the retrieved data from the one or more source systems to corresponding data elements of a data design for a computer implemented scenario on the target system, wherein the data elements of the data design have corresponding data types and a specification indicates storage of the data elements of the data design in associated database objects of the target system, and wherein one or more of the data elements of the data design are stored in the database objects on the target system having a data type different than a data type of the one or more data elements in the data design;
generate filters and transformations based on the mapping and data design and convert the retrieved data of the one or more source systems to the data types of the corresponding data elements of the data design based on the generated filters and transformations;
adjust one or more from a group of the mapping, filters, and transformations in response to detecting at least one from a group of modifications to the data design and non-conforming data received from the one or more source systems;
store the converted data for the corresponding data elements on the target system by transforming the corresponding data elements of the data design to data types of the database objects of the target system; and
retrieve information from the database objects of the target system for use by the computer implemented scenario by accessing the data elements of the data design associated with the database objects.

18. The system of claim 17, wherein the at least one processor is further configured to:
generate and execute test cases to verify the generated filters and transformations and determine an amount of the retrieved data correctly converted for the corresponding data elements of the data design in the target system.

19. The system of claim 17, wherein the computer implemented scenario includes a medical clinical trial, and the at least one processor is further configured to:
transform the data elements of the data design in the target system to a standard format used by one or more external systems and export the transformed data to the one or more external systems for processing, wherein the standard format includes one or more from a group of Clinical Data Interchange Standards Consortium Operational Data Model (CDISC ODM) and Clinical Data Interchange Standards Consortium Study Data Tabulation Model (CDISC SDTM).

20. The system of claim 17, wherein the at least one processor is further configured to:
detect the modifications to the data design and the non-conforming data received from the one or more source systems in real-time; and
provide notifications of errors due to the detected modifications and non-conforming data.

* * * * *